United States Patent
Sorenson et al.

(10) Patent No.: US 6,175,763 B1
(45) Date of Patent: *Jan. 16, 2001

(54) ELECTROTRANSPORT DRUG DELIVERY DEVICE HAVING TACTILE SIGNALING MEANS

(75) Inventors: Paul D. Sorenson, Blaine; Gary A. Lattin, Forest Lake; Larry A. McNichols, Coon Rapids, all of MN (US)

(73) Assignee: Alza Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/627,762

(22) Filed: Mar. 29, 1996

(51) Int. Cl.[7] ............................................ A61N 1/30
(52) U.S. Cl. ................................. 604/20; 604/501
(58) Field of Search .................. 604/20–21, 501; 116/205, DIG. 27

(56) References Cited

U.S. PATENT DOCUMENTS

| | | | |
|---|---|---|---|
| H71 | 6/1986 | Sorenson et al. .................. 604/20 |
| 4,297,677 | * 10/1981 | Lewis et al. . | |
| 4,301,794 | * 11/1981 | Tapper . | |
| 4,456,012 | 6/1984 | Lattin ............................. 128/420 R |
| 4,478,217 | * 10/1984 | Shimada et al. . | |
| 4,622,031 | 11/1986 | Sibalis ............................ 604/20 |
| 4,752,285 | 6/1988 | Petelenz et al. ................ 604/20 |
| 4,781,200 | * 11/1988 | Baker . | |
| 4,919,139 | 4/1990 | Brodard ........................ 128/421 |
| 4,931,046 | 6/1990 | Newman ........................ 604/20 |
| 5,013,293 | 5/1991 | Sibalis ............................. 604/20 |
| 5,036,861 | 8/1991 | Sembrowich et al. ......... 128/763 |
| 5,045,833 | * 9/1991 | Smith . | |
| 5,135,477 | 8/1992 | Untereker et al. .............. 604/20 |
| 5,135,480 | 8/1992 | Bannon et al. ................. 604/20 |
| 5,169,384 | 12/1992 | Bosniak et al. ................ 604/20 |
| 5,224,928 | * 7/1993 | Sibalis et al. . | |
| 5,415,629 | * 5/1995 | Henley . | |

FOREIGN PATENT DOCUMENTS

| | | | |
|---|---|---|---|
| 0092015 | 10/1983 | (EP) | A61N/1/30 |
| 0 461 680 A2 | 12/1991 | (EP) | A61N/1/30 |
| 2239803A | 7/1991 | (GB) | A61N/1/30 |
| WO 88/08729 | 11/1988 | (WO) | A61N/1/30 |
| WO 92/10234 | 6/1992 | (WO) | A61N/1/30 |

\* cited by examiner

*Primary Examiner*—Mark Bockelman
(74) *Attorney, Agent, or Firm*—Owen J. Bates; D. Byron Miller; Steven F. Stone

(57) ABSTRACT

An electrotransport system (20) for delivery of a drug through the skin (63) of a patient includes a tactile signal generator (36) for generating and transmitting a tactile signal to the skin of a patient upon the occurrence of an event associated with the operation of the system. The tactile signal may be an electric AC signaling current (Sr, Sp) applied through the skin, ie, an electric current different from the therapeutic electrotransport drive current. The electric signaling current is preferably a pulsed current of sufficient frequency and amplitude to allow the patient to feel it. The tactile signal may alternatively be generated by an electromechanical device in contact with the skin such as a piezoelectric vibrating element or magnetodynamic element such as a solenoid driven pin. The waveform of the tactile signaling current preferably has a zero average current component such that no net therapeutic drug is delivered by the tactile signal current. In certain cases, the tactile signaling current may contribute to electrotransport drug delivery.

27 Claims, 3 Drawing Sheets

ELECTROTRANSPORT DRUG DELIVERY DEVICE HAVING TACTILE SIGNALING MEANS

TECHNICAL FIELD

The invention relates to electrotransport devices which deliver a beneficial therapeutic agent (eg, a drug) through a body surface (eg, skin) and to indicators used to signal conditions of use or operation for such devices.

BACKGROUND ART

Electrotransport drug delivery devices have a wide range of application for transdermal delivery of therapeutic medicaments to individuals. Passive transdermal drug delivery systems employ a chemical concentration gradient and electrically-assisted (ie, electrotransport) transdermal drug delivery systems employ an electric field under control of an electronic controller to drive charged drug ions from a reservoir placed adjacent to the surface of the skin, through the skin (or a mucosal membrane) and into the bloodstream or body tissues.

Transdermal drug delivery systems are placed on the skin for some prescribed time period (eg, 24 hours) during which drug is delivered. In electrotransport devices, the transdermal drug flux, at least at certain applied current densities, is proportional to the level of applied current. The electrotransport drug flux can be controlled by controlling the magnitude and timing of the applied current. Thus, electrotransport devices afford greater control of transdermal drug flux than passive transdermal delivery systems. Because the magnitude of applied electrotransport current is typically quite low (eg, less than 150 $\mu A/cm^2$), the patients generally cannot feel the applied electrotransport current. This can create some uncertainty, at least in those electrotransport devices having no on/off indicator (or other means for signaling when the device is on and applying electrotransport current), since neither the user (patient) nor the clinician have any immediate indication that the drug is being delivered as prescribed. A malfunction of the device may not be detected during use. An example of a malfunction may simply be that the system has run out of drug and therefore cannot continue to deliver drug at the prescribed rate.

In response to these problems, many electrotransport systems incorporate visual or audible displays to communicate the status or operating conditions to the user or clinician. See for example, Maurer et al, U.S. Pat. No. 5,254,081, FIG. 3 element 70 shown as LEDs and buzzer; Bannon et al U.S. Pat. 5,135,480 FIG. 2 showing LCDs; Haak et al U.S. Pat. No. 5,246,417 showing LEDs, FIG. 5, elements 63-1 to 63-n; Sorenson, US SIR H71; DeVane UK Patent GB 2 239 803 A; and Brodard EP 0092015 October, 1983, showing a speaker for sounding an alarm.

The audible and visual displays of the prior art devices typically create lights or tones which may compete with similar lights and sound in crowded environments, creating the possibility that the display may be unnoticed. In some environments, for example, a quiet hospital ward, it may be undesirable to have disturbing or annoying lights or sounds. With visually-impaired or hearing-impaired patients, lights or sounds may not always be noticeable. Thus, there is a need for a means for notifying a patient of an electrotransport device condition without using visual or audible signals.

DISCLOSURE OF THE INVENTION

The present invention is directed to a method and apparatus for indicating an operating or other condition of an electrotransport drug delivery device. Examples of electrotransport device conditions include excessive or inadequate applied electrotransport current (which corresponds to excessive or inadequate electrotransport drug flux), excessive or inadequate skin resistance, drug exhaustion, reservoir pH, low battery strength and the like. The device includes a sensor for sensing the condition or status of the device or its operation and a tactile signal generator for generating and transmitting a tactile signal to the patient. Preferably the tactile signal is in the form of vibrations or "tingling" caused by an applied electric signaling current.

The present electrotransport drug delivery system senses and signals to the wearer (ie, the patient) (i) a condition or status of the system, and/or (ii) the occurrence of an event occurring during operation of the system. The system indicator comprises a sensor for sensing a condition or event associated with the operation of the system and a tactile signal generator for generating a tactile signal which can be sensed (ie, felt) by the patient. A controller, communicating with the sensor and the tactile signal generator, controls the tactile signal generator to generate the tactile signal when a predetermined condition or event is sensed by the sensor. The patient is thereby informed of the condition or event by sensing the tactile signal, without the need for any visual or audible signal.

The invention also includes a method of signaling a patient about the condition or status of an electrotransport drug delivery device or its operation. The method includes monitoring a condition or event associated with the operation of the system and generating a tactile signal, which signal can be felt by the patient wearing the system, when the condition or event occurs.

Different types of sensors for sensing different events and/or conditions may be used in the present invention. For example, sensors which sense (i) drug content in the donor reservoir, (ii) availability of electrochemically oxidizable or reducible species at the electrode/reservoir interface, (iii) battery voltage (iv) applied electrotransport current, (v) skin resistance, and/or (vi) pH of a donor or counter reservoir, can be used in connection with the present invention. One preferred sensor monitors the electrical resistance of the skin during transdermal electrotransport drug delivery. The sensor senses the skin resistance and the controller compares the sensed skin resistance to a predetermined acceptable skin resistance range. If the sensed skin resistance is outside the predetermined range, the controller causes the signal generator to generate a tactile signal, thereby alerting the patient to the abnormal operating condition (ie, skin resistance outside predetermined limits). Another preferred sensor is a pH sensor for monitoring the pH of a donor and/or counter reservoir in the electrotransport device and indicating when the reservoir pH exceeds, or falls below, a predetermined pH limit.

The tactile signal generator may be a piezo-electric transducer (for generating and transmitting a vibrational tactile signal) or an electric current source (eg, a battery) with appropriate electrical control circuitry to generate and transmit an electric signaling current to the patient's skin (eg, through the donor and counter electrodes which are in place on the skin).

BRIEF DESCRIPTION OF THE DRAWINGS

For a further understanding of the aspects and advantages of the present invention, reference is made to the following detailed description, taken in conjunction with the accompanying drawings, in which like parts are given like reference numerals and wherein.

MODES FOR CARRYING OUT THE INVENTION

Figure 1:
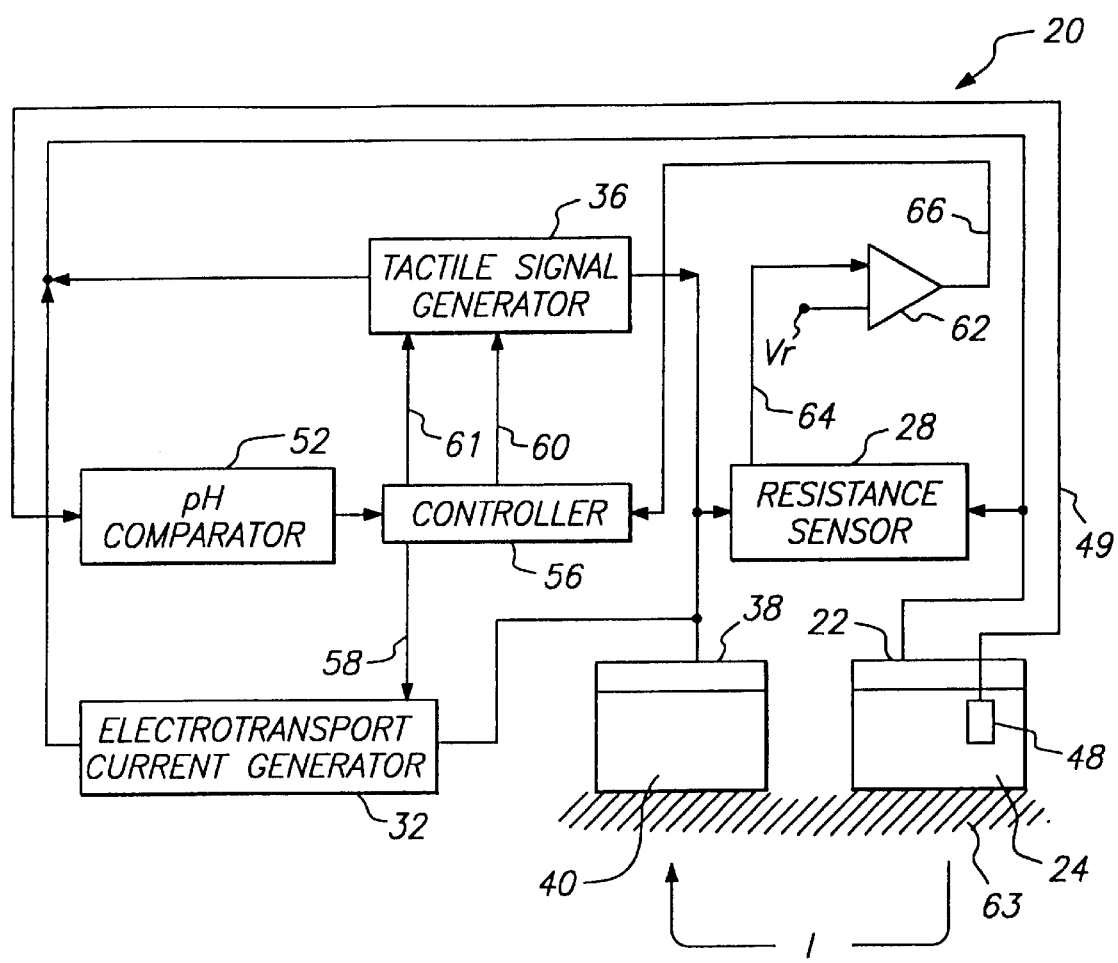
FIG. 1 is a block diagram of one embodiment of a sensor and AC tactile signal generator for an electrotransport drug delivery system in accordance with the present invention.

With reference to FIG. 1, there is shown a block diagram of an electrotransport drug delivery system, indicated generally by reference numeral 20. The system 20, as in typical electrotransport systems, includes a donor electrode 22, a counter electrode 38, and a current generator 32 for generating and controlling the magnitude, polarity, time, frequency, pulse width, and/or waveform shape (the last three being mainly in the case of a pulsing drive current) of the electrotransport drive current, shown in FIG. 1 as arrow I. The electrotransport current I delivers drug, typically in the form of drug ions, non-invasively through the patient's skin 63 and into the patient's bloodstream in order to achieve the intended therapeutic effect. The electrotransport drive current I is applied to the patient by means of a pair of electrodes 22 and 38, and respective ion-containing reservoirs 24 and 40, placed in spaced apart locations on the patient's body surface (eg, skin).

The current generator 32 includes one or more batteries (not shown) for generating the electrotransport current and electrical circuitry (not shown) for controlling its magnitude, timing, frequency, polarity, waveform shape, etc. The electrotransport current generator 32 is electrically connected to the donor electrode 22, which in turn is in electrical contact with donor reservoir (eg, in the form of a gel) containing the therapeutic agent (eg, a liquid solution of a soluble drug) to be transdermally delivered.

The counter electrode 38 is also electrically connected to the current generator 32, which in turn is in electrical contact with counter reservoir 40. Counter reservoir 40 typically contains a liquid solution of a biocompatible electrolyte salt (eg, buffered saline), but may alternatively contain a solution of the same, or a different, therapeutic agent as that contained in reservoir 24.

The reservoirs 24 and 40 are placed in ion-transmitting contact with the patient's skin 63, at spaced apart locations, for transdermal electrotransport delivery of the therapeutic agent contained in donor reservoir 24. Methods of attaching the reservoirs 24 and 40 to the skin are well known and include adhesives, adhesive overlays, adhesive sheets and strips of various contours, straps and buckles and the like. The device 20 delivers the therapeutic agent through skin 63 by means of an applied electrotransport current, I, which current is generated and controlled by generator 32.

Device 20 includes at least one sensor for sensing an event or condition associated with the operation of device 20. For purposes of illustration, device 20 is shown with two different sensors, one sensor 28 for sensing the electrical resistance of skin 63 and a second sensor 48 for sensing the pH of reservoir 24. Device 20 also includes a pH comparator 52, a controller 56 and a tactile signal generator 36. Although sensor 48 is illustrated in FIG. 1 as being positioned in the donor reservoir 24, the location of the sensor may be changed depending upon the function of the sensor (ie, the particular event or condition that the sensor is sensing). For example, a sensor located in donor reservoir 24, can be used to sense a condition relating to the composition of reservoir 24. Thus a sensor which can sense either (i) the concentration of drug remaining in reservoir 24; (ii) the pH of reservoir 24; and/or the migration of electrochemically oxidized/reduced species (eg, silver ions caused by oxidation of a silver anodic donor electrode 22; $Ag \rightarrow Ag^+ + e^-$) into reservoir 24 can be appropriately placed within reservoir 24. An optical sensor (not shown), sensitive to the color or opacity of a surface which is coated by Ag deposited during a reduction reaction as part of the electrophoretic therapy, may also be employed.

The following description concerns a sensor 48 for sensing the pH of reservoir 24. As is well known in the art (see for example et al U.S. Pat. No. 5,135,477), pH drift during operation of an electrotransport delivery device is a concern when the liquid solvent used in reservoirs 24 and 40 is water. This concern is particularly acute when the electrodes 22 and 38 are composed of materials (eg, carbon, platinum, stainless steel, etc) which are not readily oxidized or reduced at the voltages applied by the electrotransport current source. When using these "electrochemically catalytic" electrode materials, the water at the interface of the electrode and the reservoir is itself oxidized or reduced in order to pass electric current from the electrode to the reservoir. More specifically, at the anodic electrode water is oxidized ($H_2O \rightarrow 2H^+ + \frac{1}{2}O_2 + 2e^-$) resulting in the production of hydronium ions which lower reservoir pH. At the cathodic electrode water is reduced ($H_2O + e^- \rightarrow OH^- + \frac{1}{2}H_2$) resulting in the production of hydroxyl ions which raise reservoir pH.

Donor reservoir pH must be closely monitored when delivering drugs whose solubility, and/or degree of ionization has a high dependency on pH. In addition, donor and counter reservoir pH should be monitored to guard against excessively low or high pH's which can result in irritation of the skin sites in contact with the reservoirs. This pH monitoring is accomplished by the sensor 48 which senses the pH of the donor reservoir 24 and provides a signal 49 to pH comparator 52. The comparator 52 provides a pH limit signal to controller 56 when the pH in the donor reservoir 24 falls outside a predetermined acceptable range.

In addition to the pH sensor 48, device 20 is shown with a resistance sensor 28 which is used to sense the voltage drop across the electrodes 22 and 38 and thereby indirectly sense the electrical resistance of skin 63. The provision of the two separate sensors 28 and 48 within device 20 is optional and those skilled in the art will readily appreciate that electrotransport devices having only a single sensor, as well as those devices having a plurality of sensors, are within the scope of the invention. The resistance sensor 28 is a conventional voltage measuring device, such as a volt meter or other known apparatus for measuring the voltage drop (ΔV) across the electrodes 22 and 38. The skin resistance ($R_{skin}$) can then be determined from the applied electrotransport current I using Ohm's law (ie, $R_{skin}=\Delta V/I$). In addition to conventional volt meters, other resistance and/or impedance sensing circuits such as a circuit which applies a constant AC current, or an AC resistance bridge with a metering output and the like, may also be used. Such a circuit provides a constant AC sensor current and measures the resulting AC sensor voltage between the electrodes. The AC current from the sensor preferably has a frequency and magnitude which results in no net drug delivery via electrotransport.

For humans, the steady-state electrical resistance of the skin is generally in the range of about 500 ohms to about 50 kohm. For extremely dry and callous skin, a steady-state electrical resistance of 300 kohm or more is possible.

The resistance sensor 28 provides an output signal 64 to comparator 62. The signal output 64 is proportional to the measured voltage drop between the electrodes 22 and 38. The comparator 62 compares the signal 64 with a reference voltage Vr provided by a reference voltage source such as a voltage divider or band gap reference device (not shown). The comparator 62 produces an output signal 66 to controller 56, when the signal 64 differs significantly from reference voltage Vr. The comparator 62 may be set to trigger the output signal 66 upon sensing a skin resistance that is either too high or too low.

The selection of the reference voltage Vr depends primarily upon the desired level of electrotransport drive current I, since skin resistance is assumed to be within a narrow acceptable range for the particular type of patients (eg, human patients) to be treated. To some degree, the reference voltage Vr is a function of the type of electrodes/reservoirs used, and the materials from which they are constructed, since any resistance provided by the electrodes and reservoirs will also be sensed by the resistance sensor 28. The reference voltage Vr may be a minimum voltage limit. If the sensed voltage drop across the electrodes 22,38 is less than Vr, the skin is assumed to have too low an electrical resistance (ie, cut or abraded skin), and the device is then switched to a signaling mode. In general, if the sensed voltage drop across the electrodes indicates that the skin resistance is less than 10 kohm/cm$^2$, the skin is considered to have abnormal (ie, too low) electrical resistance and the device is switched to a signaling mode. Alternatively, the reference voltage Vr may be a maximum voltage limit. If the sensed voltage drop across the electrodes exceeds Vr, the device is assumed to have become dislodged from the patient's skin (or alternatively, the patient's skin is too resistive for acceptable electrotransport drug delivery). In general, if the sensed voltage drop across the electrodes indicates that the skin resistance is greater than about 500 kohm/cm$^2$, the skin is considered to have abnormal (ie, too high) electrical resistance and the device is switched to a signaling mode.

The controller 56 communicates with the current generator 32 through connection 58. The controller 56 communicates with the tactile signal generator 36 through connections 60 and 61.

Figure 2:
FIG. 2 illustrates a tactile signaling current waveform which may be produced by the tactile signal generator of the system shown in FIG. 1.

In the normal operation of device 20, the reservoirs 24 and 40 are attached to the skin 63 and the current generator 32 begins delivering electrotransport current, I (shown schematically by the arrow in FIG. 1), through electrodes/ reservoirs 22, 24 and 38, 40. If the attachment of the electrodes/reservoirs 22, 24 and 38, 40 to the skin 63 is satisfactory, and the electrical resistance of skin 63 is within a normal range, and the pH of the donor reservoir 24 is within the predetermined pH limits, the delivery of current I proceeds normally. If the contacts of either the electrodes/ reservoirs 22, 24 and/or 38, 40 to the skin 63 are poor, or alternatively if the contacts between the electrodes/ reservoirs 22,24 and 38,40 and the skin 63 are good but the patient's skin 63 has an abnormally high (or an abnormally low) electrical resistance, such that the resistance calculated from the voltage drop across the electrodes 22, 38 (which voltage drop is measured by the resistance sensor 28) differs significantly from the predetermined reference voltage Vr, then the output signal 66 of comparator 62 will activate the controller 56. The controller 56 responds to the output signal 66 by sending a signal through connection 60 which causes tactile signal generator 36 to generate an alternating voltage signal which drives a first signaling current Sr to the electrodes 22, 38 and through the skin 63. The amplitude and waveform shape of signaling current Sr are selected so that the patient can feel the applied signaling current Sr, ie the signaling current Sr provides a tingling sensation to the patient. Preferably, the waveform shape of signaling current Sr is selected so as to have no significant effect on the amount or rate at which drug is delivered through skin 63. One preferred waveform shape for signaling current Sr is illustrated in FIG. 2.

In the case where the resistance sensor 28 is monitoring for abnormally high voltage drop/skin resistance, the signaling current Sr is activated to notify the patient that the skin resistance is too high and/or the mounting of either or both of the electrodes/reservoirs 22, 24 and 38, 40 is inadequate and should be adjusted. The patient then can reposition or refasten the electrodes/reservoirs 22, 24 and 38, 40 on the skin 63 until the resistance measured by the sensor 28 is within the predetermined range and the signal 64 falls below the reference voltage Vr. The comparator 62 then disables the output signal 66, the controller 56 deactivates the connection 60 and the tactile signal generator 36 turns off the signalling current Sr. The delivery of the therapeutic electrotransport current I then proceeds as before. If repeated repositioning of electrodes/reservoirs 22, 24 and 38, 40 fails to bring the voltage drop/skin resistance measured by resistance sensor 28 down to an acceptable range, the patient would be instructed to discontinue attempts to reposition the electrodes/reservoirs 22, 24 and 38, 40 and to consult the therapist or physician.

Alternatively, in the case where the reference voltage is a minimum voltage corresponding to a minimum acceptable skin resistance and the resistance sensor 28 is monitoring for abnormally low voltage drop/skin resistance, the signaling current Sr is activated to notify the patient that the skin resistance of the skin site(s) to which reservoirs 24 and/or 40 have been applied is too low the the electrodes/reservoirs 22, 24 and 38, 40 should be repositioned on another skin site. The patient then can reposition or refasten the electrodes/ reservoirs 22, 24 and 38, 40 on the skin 63 until the resistance measured by the sensor 28 is within the predetermined range and the signal 64 falls above the reference voltage Vr. The comparator 62 then disables the output signal 66, the controller 56 deactivates the connection 60 and the tactile signal generator 36 turns off the signalling current Sr. The delivery of the therapeutic electrotransport current I then proceeds as before.

If repeated repositioning of electrodes/reservoirs 22, 24 and 38, 40 fails to bring the voltage drop/skin resistance measured by resistance sensor 28 up to an acceptable range, the patient would be instructed to discontinue attempts to reposition the electrodes/reservoirs 22, 24 and 38, 40 and to consult the therapist or physician.

Figure 3:
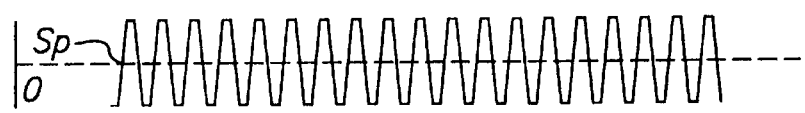
FIG. 3 illustrates another tactile signaling current waveform having a frequency higher than the frequency of the waveform shown in FIG. 2.

In the case where the pH in the donor reservoir 24 falls outside the predetermined range, the comparator 52 responds to the signal 49 by outputting the limit signal 54. The controller 56 responds to the limit signal 54 by activating the signal on connection 61. The tactile signal generator 36 responds to the signal on connection 61 by outputting a second signaling current, Sp, to the electrodes 22 and 38. The waveform shape of signaling current Sp is illustrated in FIG. 3. The frequency, fp, and amplitude, Ap, of the signaling current, Sp, is selected to impart a different tactile sensation in the skin 63 (ie, a tactile sensation which is different and distinguishable (ie, by the patient) from the tactile sensation imparted by signaling current Sr) in order to notify the patient that the pH of the donor reservoir 24 is outside of a predetermined acceptable (eg, acceptable from a skin irritation and/or drug solubility standpoint) range. The patient then may remove the electrodes/reservoirs 22, 24 and 38, 40 and replace them with fresh electrodes/reservoirs for reattachment and continued therapy as prescribed.

As shown in FIGS. 2–5, the waveform shapes of signaling currents Sr and Sp have a positive phase and a negative phase, ie they are alternating currents (AC). Most preferably the positive phase equals the negative phase such that the application of the signaling currents Sr and/or Sp produce no net direct current (DC). An absence of any net DC current in the signalling currents Sr and Sp ensures that the signaling currents have no net effect on the amount or rate of electrotransport drug delivery to the patient.

As shown in FIG. 2, tactile signaling current Sr has a constant peak amplitude and frequency. As shown in FIG. 3, signaling current Sp has the same constant peak amplitude as current Sr, but a different frequency. The amplitudes and frequencies of signaling currents Sr and Sp are selected to be sufficiently different, so that the tactile sensation produced by these two currents will be perceptibly different, ie the patient will be able to feel the differences in the two currents and be able to distinguish one from the other.

Figure 4:
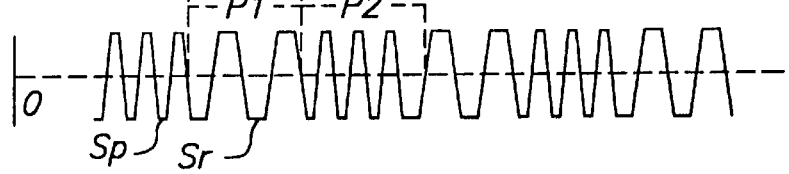
FIG. 4 illustrates a repetitive sequence of tactile signaling current pulses of a first frequency and repetition rate, and a second frequency and repetition rate.

FIG. 4 illustrates a tactile signaling current comprised of alternating periods of current Sp and current Sr. Thus, the signaling current of FIG. 4 has alternating periods, P1 and P2, of different frequencies. The length of the periods, P1 and P2 may also be varied so as to indicate different events or conditions.

Figure 5:
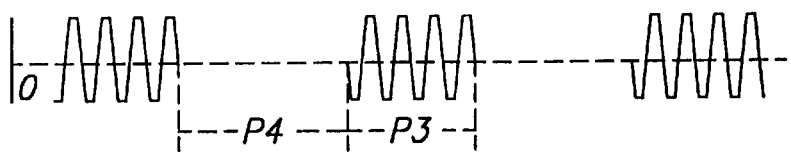
FIG. 5 illustrates a repetitive sequence of tactile signaling current pulses of a different frequency and repetition rate than that of FIG. 4.

FIG. 5 illustrates a tactile signaling current having alternating periods, P3, of tactile signal interspersed with the periods, P4, with the absence of tactile signal. Various combinations of such tactile signals or the like can be provided in alternate embodiments of the present invention, to indicate different conditions or events to the patient using the device.

The peak amplitudes of the different tactile signaling currents may be constant with time, or may be caused to vary during the pulse period. For example, the amplitudes may vary from a zero or low value to a higher value, ie sloped, or inversely from high to low, as desired. Such variations may be implemented by conventional circuit means well known in the art. See for example, Brodard, U.S. Pat. No. 4,919,139.

Each pulse of signaling current Sr and/or Sp preferably has a peak amplitude of about 25 to 150 mA with a pulse width of about 1 $\mu$sec to 2 msec, with the longer pulse widths being used with the lower peak currents in these two ranges, and vice versa. As an upper limit, each pulse of signaling current Sr and/or Sp should deliver less than about 75 micro-Coulombs ($\mu$C) of charge, and preferably about 5 to 50 $\mu$C of charge. The pulse durations, pulse repetition rate and signal frequencies for the tactile signals are generally of low to moderate repetition rates and frequency range. Pulse rates as low as 0.5 cycles per second (cps) to several hundred cps may be used. In the case of pulsed AC tactile signaling currents, the duration of the pulse may last for a number of cycles, eg, the frequency of the tactile signal during the pulse width would be several or many times higher than the pulse repetition rate. In general, pulsed AC tactile signals having a frequency in the range of about 10 to 70 Hz may be used. Preferred frequencies for the signaling currents are those frequencies commonly used with transcutaneous electrical nerve stimulation (TENS) since they are AC signals which are well tolerated by human patients and which deliver no net drug.

With reference to FIGS. 4 and 5, there is shown pulsing AC signaling currents. The preferred range of peak amplitude and frequency of the signaling currents is determined by what is required for the patient to feel. The peak current density (ie, peak current amplitude divided by the skin contact area of the smallest of the two reservoirs 24,40) should be high enough for the patient to feel. The transcutaneous electrical nerve stimulation (TENS) frequency range is preferred since TENS currents are well tolerated by human patients and further are AC signals that deliver no net drug via electrotransport.

For the case of pulsed tactile signals, the waveform shape during the pulse may be sinusoidal, piece-wise linear or highly non-linear. See, for example Lattin U.S. Pat. No. 4,456,012, FIG. 3 and FIG. 5.

Figure 8:
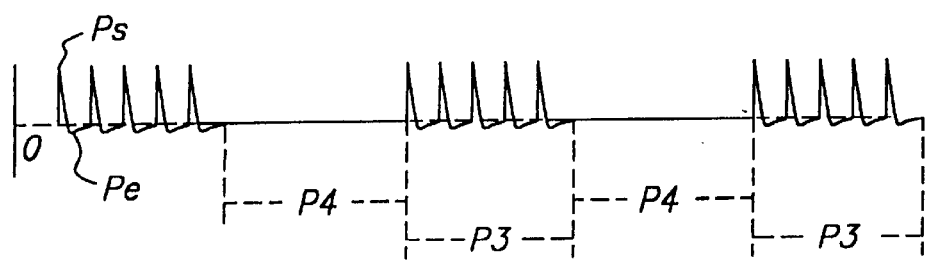
FIG. 8 illustrates another tactile signaling current waveform which can be used in the present invention.

FIG. 8 illustrates a biphase tactile signaling current waveform having a markedly non-linear spiked positive phase Ps followed by a decaying exponential negative phase Pe, such that the net current delivered over the two phases, Ps and Pe, is zero. This is typical of an AC coupled signal provided by a pulse transformer connection (not shown) to the electrodes 22 and 38.

Generally, the tactile signal pulse widths may be from about 20 $\mu$sec up to about 5 msec. A preferred range of tactile signal pulse widths is from about 50 to about 1000 $\mu$sec.

All of the tactile signals shown in FIGS. 2–5 and FIG. 8 will deliver little or no net drug into the skin of a patient via electrotransport even though the signaling current is being applied through the drug delivery electrodes/reservoirs 22, 24 and 38, 40. This is because the amount of applied "positive" signaling current is equal to the amount of "negative" signaling current. In other words, all of the AC signaling current waveforms shown in FIGS. 2–5 and 8 have an average DC current of zero and thus will not introduce pharmaceutically significant amounts of drug from the reservoir 40 into the patient.

It is not absolutely necessary for the tactile signaling currents Sr and Sp to have little or no effect on electrotransport drug delivery however. In certain situations it might actually be more preferred to have the signaling current contribute to the amount and/or rate of drug delivered via electrotransport to the patient. For example, in the case where the sensor is sensing the concentration of drug remaining in the donor reservoir 24, it may be desirable, once the drug concentration falls to a level at which electrotransport drug flux becomes dependent on the concentration of drug remaining in the donor reservoir, to have the signaling current not only signal the patient to replace the donor reservoir with a fresh donor reservoir, but also to have the signaling current have a net augmenting effect on the total electrotransport drive current I so as to compensate for the decrease in electrotransport drug flux which would otherwise occur due to the falling concentration of drug in the donor reservoir.

In the case that both monitored conditions occur simultaneously, ie, the load resistance between the electrodes/reservoirs 22, 24 and 38, 40 is outside of a predetermined acceptable range (eg, because of abnormally high electrical resistance of skin 63 and/or poor electrical contact between the skin 63 and the electrodes/reservoirs 22, 24 and 38, 40), and the pH is outside of the predetermined acceptable range, the controller 56 is configured to alternately select connection 60 and 61 so that alternate signaling currents Sr and Sp are delivered to the patient's skin 63. This is seen with regard to FIG. 4, in which signaling current waveform, Sr, is alternated with signaling current waveform, Sp. Sp and Sr may be of widely differing frequencies, repetition rates and/or amplitudes to clearly signal to the patient that both conditions (ie, off-specification skin resistance and off-specification reservoir pH) are occuring simultaneously.

Signaling currents Sr and Sp may be differentiated from the applied therapeutic (ie, electrotransport drug delivery) current I in several ways. The therapeutic electrotransport current I is generally either a straight DC current, or a very low frequency (ie, less that 50 Hz) pulsed DC current, having a peak current/current density which is too low (ie, low magnitude) to be felt by the patient. Thus, the primary "differentiation" between the therapeutic current and the signaling current is the patient's ability to feel the signaling current waveforms Sr and Sp versus the patient's inability to feel the drug delivery current I. However, in those drug delivery regimens requiring quick delivery of drug at high rates (eg, delivery of a 5HT3 receptor antagonist at onset of a migraine in order to prevent the occurrence of the migraine), the applied therapeutic current I may be above the sensation threshold level. In these cases, the "differentiation" can be provided by having (i) a DC (non-pulsing) therapeutic current and a pulsing signaling AC current, or (ii) a pulsed DC therapeutic current in combination with AC signaling currents of widely differing amplitudes and or repetition rates, eg, a signaling current having a higher peak amplitude than the peak amplitude of the therapeutic current and/or different frequencies or repetition rates.

Electrotransport therapy with the present invention has been discussed in relation to transdermal drug delivery. It should be understood that this invention is equally applicable to electrotransport drug delivery through other body surfaces such as mucosal membranes, ie, nasal passages, the oral cavity and the like. Mucosal membranes have different (ie, lower) resistance/impedance characteristics than skin and therefore require lower voltage levels to generate the same tactile signaling currents. Adjustment to accommodate these differences can be made through routine experimentation following the teachings herein relative to skin.

The ability of patients to differentiate between the electrotransport drive current I and the tactile signaling currents will vary from patient to patient due to differing abilities to feel applied electric current, skin characteristics, and the specific skin site to which the current is applied. Some patients may have skin which is unusually dry and/or callous and therefore of much higher electrical resistance than most patients. For these patients, it may be desirable to provide an adjustment mechanism to provide higher driving voltages to achieve the necessary signaling current levels.

The logic involved with the operation of system 20 is as follows. In the idle condition, no electrotransport current is delivered from current generator and controller 32. When the electrodes/reservoirs 22, 24 and 38, 40 are attached to the skin 63, and the electrotransport delivery current I is started (eg, automatically or by means of a manually activated switch), the system 20 changes from an idle state to an electrotransport therapeutic agent delivery state characterized by the generator 32, delivering electrotransport current I to the electrodes/reservoirs 22, 24 and 38, 40 and through the skin 63.

Current delivery continues as long as there is no occurrence of an "off-specification" event or condition, which in the FIG. 1 device is characterized by the donor reservoir 24 pH and/or the voltage drop across electrodes 22 and 38 falling outside predetermined acceptable ranges. If such an event or condition occurs, the system 20 changes to a tactile signal generation state by activating the tactile signal generator 36. Optionally, the controller 56 also deactivates the current generator 32 thereby stopping the delivery of the therapeutic electrotransport current I. The tactile signal generation state continues as long as the event or condition persists.

If the event or condition stops (ie, if the voltage drop across the electrodes and/or the pH of the donor reservoir 24 returns to a level within the predetermined acceptable range (s)) the tactile signal generation ceases and, if the current I had been interrupted during the signal generation, then the system 20 returns to delivery of electrotransport current I.

Figure 6:
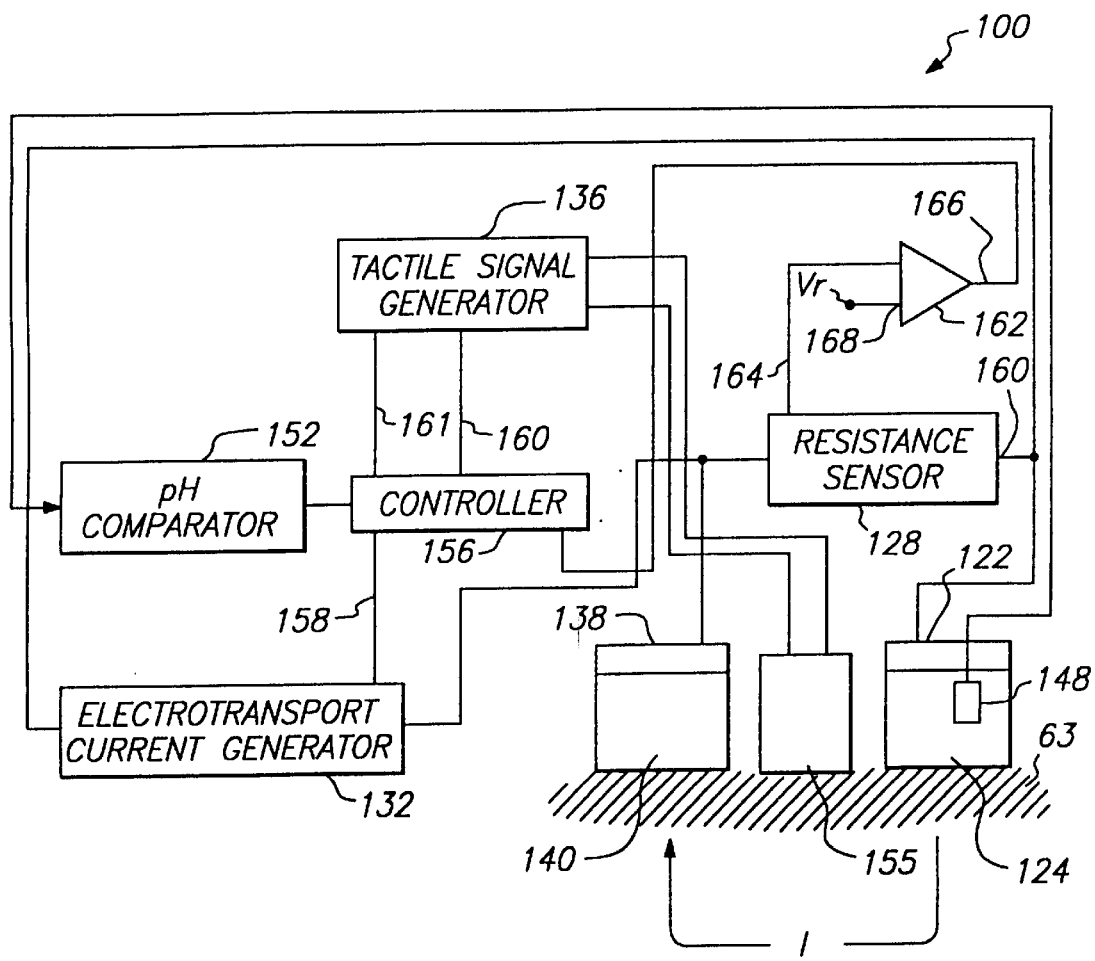
FIG. 6 is a block diagram of another electrotransport delivery system having an alternate event indicator including an electromechanical device for tactile signaling.

With reference to FIG. 6 there is shown an electrotransport delivery system 100 which uses an electromechanical tactile signal generator in accordance with this invention. The system 100 includes spaced apart donor and counter electrodes/reservoirs 122,124 and 138,140. System 100 also includes a resistance sensor 128, a comparator 162, a tactile signal generator 136, a pH sensor 148, a pH comparator 152, a controller 156, and an electrotransport current generator 132.

The donor electrode 122 is electrically connected to a donor reservoir 124 containing a liquid solution of a therapeutic agent (eg, a drug) in a form suitable for electrotransport delivery. The counter electrode 138 is electrically connected to a counter reservoir 140 containing a biocompatible salt solution. The donor reservoir 124 and counter reservoir 140, respectively, are affixed to the skin 63 as previously described. Electrode 122 is electrically connected to the sensor 128 and the current generator 132. The counter electrode 138 is electrically connected to the sensor 128 and to the current generator 132.

Unlike the system 20 shown in FIG. 1, system 100 includes an electromechanical signal transmitter 155. The electromechanical signal transmitter 155 may be a piezoelectric transducer such as those used in headphones, microphones, tweeters, heart pacers, sonar transducers, alarms and the like. Piezoelectric ceramics such as barium titanate, lead metaniobate, and lead titanate zirconate solid solution ceramics are particularly useful in the low frequency range. The transmitter 155 may be mounted in close proximity to the electrodes/reservoirs 122,124 and 138, 140 or may be remotely located, by separate mounting means (not shown), in contact with the skin 63. Appropriate coverings and seals to encapsulate the tactile signal transmitter 155 and separate it from the electrodes/reservoirs 122, 124 and 138, 140 may be used to prevent exposure of the skin 63 to direct contact with the piezo-electric transducer element in transmitter 155. Piezoelectric sonic transducers may be used in thickness and face shear, thickness and length or planar expansion modes. Flexing type piezoelectric elements can handle larger motions and smaller forces than single plates. Alternatively, the electromechanical transmitter 155 may be a magnetodynamic device such as a solenoid driven pin, coil driven speaker or the like. An alternative electromechanical transmitter 155 is a miniature electromagnetic transducer such as a moving-coil, moving iron, electrostatic or magnetostrictive transducer or a plurality of solenoid driven pluralities of pins or the like.

The tactile signal transmitter 155 is connected to the signal generator 136. The controller 156 is electrically connected to the tactile signal generator 136 by connections 160, 161. The pH sensor 148 is positioned in the donor reservoir 124 and is electrically connected to the pH comparator 152. The pH comparator 152 is electrically connected to the controller 156. Another output 158 of the controller 156 electrically connects to the current generator 132.

Another input of controller 156 is driven by the output signal 166 of comparator 162. A sense input of comparator 162 is electrically connected to an output of the resistance sensor 128. A reference input of comparator 162 connects to a reference voltage Vr as described earlier in connection with FIG. 1.

The controller 156 may be a microcomputer control system incorporating a stored program in read only memory (ROM) or a hardwired logic system comprised of conventional logic elements such as standard or custom MOS integrated circuits or the like. One chip microcomputers having programmable memories and programmable dedicated I/O connections suitable for such control are well known in the art.

The electrotransport current generator 132 may be a controllable constant current source or a controllable voltage source supplied by a primary or rechargeable battery. Such controllable current sources are well known in the art. Commercial step up voltage and current controllers such as the "MAX1771" and the "MAX1773" made by Maxim Integrated Products, Inc of Sunnyvale, Calif. are suitable for converting and controlling the low battery voltage of primary cells into controllable electrotransport currents and/or voltages.

The operation of system 100 is as follows. Once the system 100 is connected to an internal power source (not shown) such as a battery, the system 100 is initialized to an idle state. After positioning the electrodes/reservoirs 122, 124 and 138,140 and the tactile signal transmitter 155 in contact with the desired location of the patient's skin, the system 100 is activated (eg, automatically or upon the closing of a manually activated switch) thereby starting electrotransport current I delivery.

Therapeutic electrotransport current I will continue to be delivered until either of one of two events occur causing transition from the electrotransport current delivery state to a signaling state.

A first event, designated E1 (but not show in the Figures), corresponds to an out-of limit resistance detection from the resistance sensor 128 and the comparator 162. The comparator output 166 activates the controller 156.

A second event, designated E2 (also not shown in the Figures), corresponds to an out-of-limit pH detection from the pH sensor 148 and the pH comparator 152. The pH comparator 152 activates the controller 156.

Activation of controller 156 by means of either (i) the pH comparator sensing an "off-specification" pH in reservoir 124, or (ii) the resistance sensor 128 sensing an "off-specification" skin resistance, initiates a timer, for example a built-in timer function in a micro-computer included in the controller 156.

After the timer is set, the system 100 will transition to one of three signal generation states, designated states S1, S2, and S3, depending on the condition of the exception event. If the event condition is E1 and not E2, the system 100 will transition to the signal generation state S1. If the event condition is E1 and E2, the system will transition to the signal generation state S2. If the event condition is E2 but not E1, the system will transition to signal generation state S3.

The three signal generation states S1, S2 and S3 correspond to different frequency and signal amplitude tactile stimuli provided from the tactile signal generator 136. Referring to FIGS. 2–4, the controller 156 activates the tactile signal generator 136 to output pulsing current waveform Sr for S1, pulsing current waveform Sp for S2, and alternating current waveforms Sr, Sp for condition S3, by applying one of three different logic level combinations on the connections 160 and 161.

The tactile signal transmitter 155, in contact with the skin 63, causes one of the three different signals to provide one of three different tactile sensations in the skin of the patient thereby notifying the patient of the present exception condition.

At the end of the preset time, the timer causes the system 100 to transition from the existing stimulus state, S1, S2, or S3, back to the electrotransport current delivery state. If the exception event or events are still true, ie, E1 or E2, the exception events will cause the timer to be set again, repeating the cycle until the system 100 is turned off, or the exception condition is cleared.

Other state conditions may be defined for the application of tactile signaling such that, therapeutic current I may be continued simultaneously with tactile signaling as desired.

Figure 7:
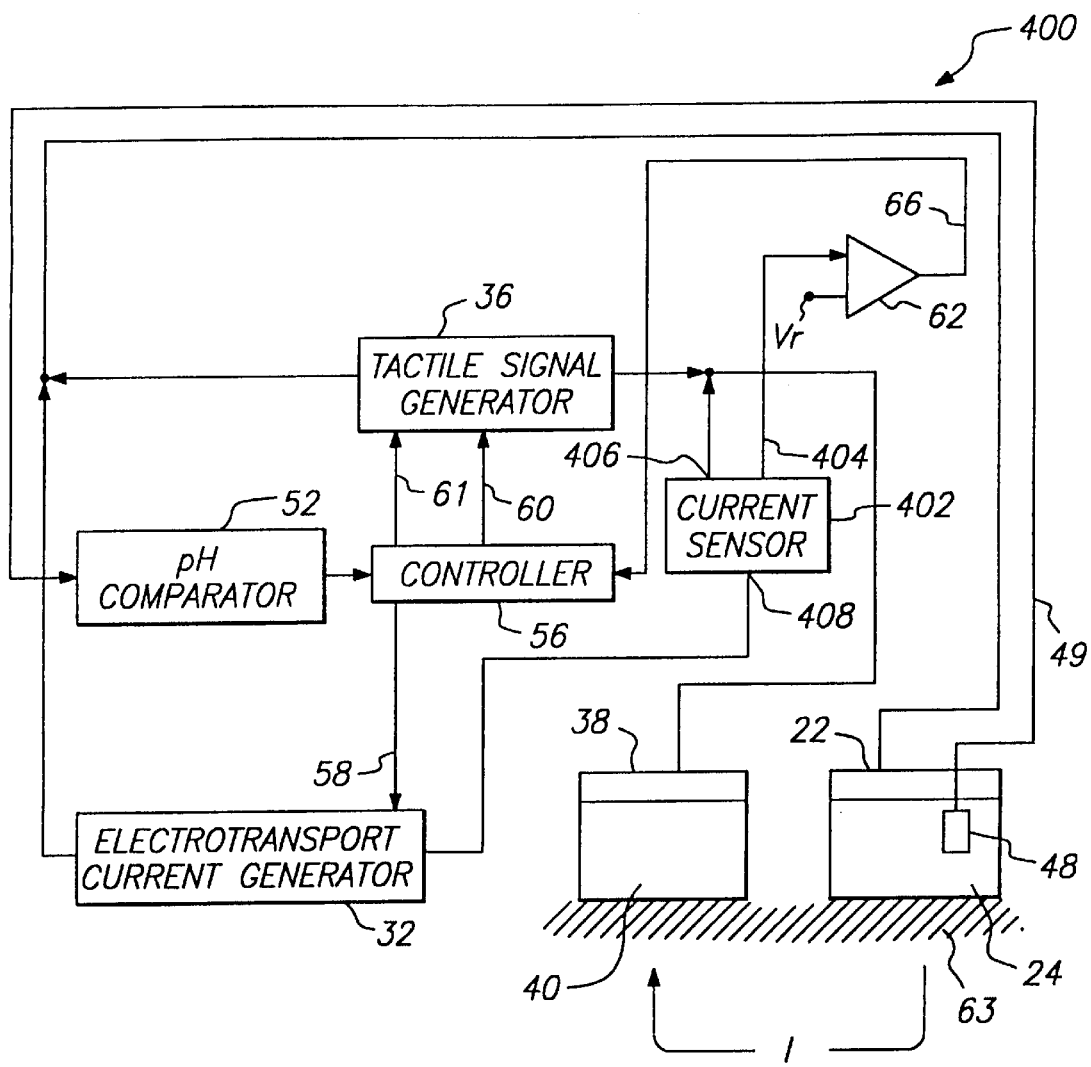
FIG. 7 is a block diagram of yet another electrotransport delivery system having an alternate event indicator including a current sensor coupled to a tactile signaling apparatus in accordance with this invention.

An alternative electrotransport device 400 is shown in FIG. 7 with elements common to the system 20 of FIG. 1 in which like elements have like reference numbers. The system 400 includes a current sensor 402 responsive to electrotransport current I. The current sensor 402 is in series between the electrotransport current generator 32 and one electrode/reservoir 38, 40 in contact with the patient's skin 63. Electrotransport drive current I is applied by the current generator 32, through the current sensor 402, to another electrode/reservoir 22, 24 in contact with the patient's skin proximal to electrode/reservoir 22, 24.

Sensor 402 senses the applied electrotransport current I and generates a voltage output 404, proportional thereto. The output 404 is transmitted to the comparator 62. Another input of comparator 62 is connected to a reference voltage reference Vr. In the event that there is an excursion of the current, I, such that I differs from the desired therapeutic current level by an amount sufficiently different from a reference value as established by the reference voltage Vr, the comparator 62 outputs the signal 66 to controller 56. Controller 56 then activates the tactile signal generator 36 to generate a tactile signaling current Sr (as shown in FIGS. 2–5) to flow. The patient is thereby alerted that the therapeutic current is incorrect, allowing appropriate action to be taken.

Other conditions or events which may be sensed by appropriate sensors, to initiate a tactile signal for alerting the patient include: depletion of drug from the donor reservoir; low battery voltage; migration of silver ions, from oxidation of a silver anode, into a reservoir in order to prevent discoloration of the skin; and depletion of oxidizable/reducible electrode material by measuring voltage drop across the electrode/reservoir interface as discussed in Petelenz et al U.S. Pat. No. 4,752,285.

Other embodiments of the invention may incorporate other exception conditions such as unacceptable drug delivery rate (ie, too high or too low), exhaustion of one or more of the drug reservoirs, or the like by including additional sensors in contact with the skin or by measuring other body parameters.

While the foregoing detailed description has described several embodiments of the electrotransport system in accordance with this invention, it is to be understood that the above description is illustrative only and not limiting of the disclosed invention. It will be appreciated that it would be possible for one skilled in the art to modify the shape, dimensions and materials of the device, or to include or exclude various elements within the scope and spirit of this invention. Thus the invention is to be limited only by the following claims.

What is claimed is:

1. An electrotransport drug delivery system which can signal, to a patient wearing the system, an occurrence of an event or condition associated with operation of the system, comprising:

an electrotransport drug delivery system including a pair of electrodes, at least one of which having a reservoir attached thereto, through which an electrotransport drug delivering current is applied to the patient;

a sensor connected to the system for sensing an event or condition associated with the operation of the system;

a tactile signal generator connected to the system, responsive to the sensor, for generating and transmitting an electric tactile signaling current through the pair of electrodes to the patient, the signaling current having a magnitude and waveform shape which is capable of being felt by the patient and which delivers little to no net drug to the patient.

2. The system of claim 1, including a controller, communicating with the sensor and the tactile signal generator, for controlling the signal generator to generate the tactile signal when the event or condition is sensed by the sensor.

3. The system of claim 1, wherein the sensor senses an event or condition selected from the group consisting of reservoir pH, skin resistance, battery voltage, applied electrotransport current, Ag+ ion concentration, hydronium (H+) ion concentration, hydroxyl (OH-) ion concentration.

4. The system of claim 2, including a comparator for comparing the sensed event or condition with a predetermined value therefor.

5. The system of claim 1, wherein the event or condition comprises skin resistance and the sensor includes a resistance sensor for sensing voltage drop responsive to skin resistance across donor and counter electrodes.

6. The system of claim 1, wherein the event or condition comprises applied electrotransport current and the sensor includes an applied electrotransport current sensor.

7. The system of claim 1, wherein the sensor is capable of sensing a plurality of different types of events or conditions.

8. The system of claim 7, wherein the tactile signal generator is capable of generating and transmitting a plurality of different tactile signaling currents to the patient, each tactile signaling current corresponding to one of said plurality of different events or conditions.

9. The system of claim 1, wherein the electric tactile signaling current has a waveform which delivers drug to the patient by electrotransport.

10. The system of claim 1, wherein the electric tactile signaling current has alternating periods of different length.

11. The system of claim 1, wherein the electric tactile signaling current is an alternating current.

12. The system of claim 1, wherein the electric tactile signaling current has alternating periods of different frequency.

13. The system of claim 1, wherein the electric tactile signaling current has alternating periods of different amplitude.

14. The system of claim 1, wherein the electric tactile signaling current has a waveform which delivers substantially no drug to the patient by electrotransport.

15. A method for signaling a patient of an occurrence of an event or condition associated with operation of an electrotransport drug delivery system worn by the patient, the system including a pair of electrodes, at least one of which having a reservoir attached thereto, through which an electrotransport drug delivering current is applied to the patient, the method comprising:

sensing an event or condition associated with operation of the electrotransport drug delivery system;

generating an electric tactile signaling current in response to the sensed event or condition; and transmitting the tactile signaling current to the patient through the pair of electrodes, the signaling current having a magnitude and waveform shape which is capable of being felt by the patient and which delivers little to no net drug to the patient.

16. The method of claim 15, wherein the sensed event or condition is selected from the group consisting of reservoir pH, skin resistance, battery voltage, and applied electrotransport current.

17. The method of claim 15, including comparing the sensed event or condition with a predetermined value therefor.

18. The method of claim 15, wherein the event or condition comprises skin resistance and the sensing comprises sensing voltage drop across donor and counter electrodes.

19. The method of claim 15, wherein the event or condition comprises applied electrotransport current.

20. The method of claim 15, including sensing a plurality of different types of events or conditions.

21. The method of claim 20, including generating and transmitting a plurality of different tactile signaling currents to the patient, each tactile signaling current corresponding to one of said plurality of different events or conditions.

22. The method of claim 15, wherein the tactile signaling current is an alternating current.

23. The method of claim 15, wherein the tactile signaling current has alternating periods of different length.

24. The method of claim 15, wherein the tactile signaling current has alternating periods of different frequency.

25. The method of claim 15, wherein the tactile signaling current has alternating periods of different amplitude.

26. The method of claim 15, wherein the tactile signaling current has a waveform which delivers substantially no drug to the patient by electrotransport.

27. The method of claim 15, wherein the tactile signaling current has a waveform which delivers drug to the patient by electrotransport.

* * * * *